(12) United States Patent
Dubey et al.

(10) Patent No.: US 9,675,657 B2
(45) Date of Patent: Jun. 13, 2017

(54) ROLE OF AN HERBAL FORMULATION IN THE PREVENTION AND MANAGEMENT OF AGE RELATED NEURODEGENERATIVE DISORDERS WITH SPECIAL REFERENCE TO SENILE DEMENTIA

(75) Inventors: Govind Prasad Dubey, Benares (IN); Aruna Agrawal, Benares (IN); Nirupama Dubey, Kattankulathur (IN); Shipra Dubey, Kattankulathur (IN); Rajesh Dubey, Kattankulathur (IN); Samathanam Mercy Deborah, Benares (IN)

(73) Assignee: SRM UNIVERSITY, Kattankulathur (IN)

(*) Notice: Subject to any disclaimer, the term of this patent is extended or adjusted under 35 U.S.C. 154(b) by 197 days.

(21) Appl. No.: 13/206,298

(22) Filed: Aug. 9, 2011

(65) Prior Publication Data

US 2012/0034324 A1 Feb. 9, 2012

(30) Foreign Application Priority Data

Aug. 9, 2010 (IN) .......................... 2271/CHE/2010

(51) Int. Cl.
*A61K 36/35* (2006.01)
*A61K 36/9066* (2006.01)
*A61K 36/68* (2006.01)
*A61K 36/80* (2006.01)
*A61K 36/84* (2006.01)

(52) U.S. Cl.
CPC .............. *A61K 36/80* (2013.01); *A61K 36/84* (2013.01); *A61K 36/9066* (2013.01)

(58) Field of Classification Search
None
See application file for complete search history.

(56) References Cited

PUBLICATIONS

Aggarwal et al. (2009) Inter. J. Biochem. Cell Biology 41, pp. 40-59.*
Ho et al. (2010) Aging Research Reviews 9, 354-362.*
Phrompittayarat et al. (2007) Naresuan University Journal 15(1); 29-34.*
Roth et al. (1998) J. Nat. Prod. 61, 542-545.*
Russo et al. (2003) Phytother. Res. 17, 870-875.*
Singh et al. (2006) Chromatographia 63, Feb. (No. 3/4) pp. 209-213.*
Suhaj, M. (2006) Journal of Food Composition and Analysis 19, pp. 531-537.*
Tohda et al. (2006) eCAM 3(2) 255-260.*
Calabrese et al. (2008) The Journal of Alternative and Complementary Medicine vol. 14, No. 6, pp. 707-713.*
Chainani-Wu (2003) The Journal of Alternative and Complementary Medicine vol. 9, No. 1, pp. 161-168.*
Govindarajan et al. (2005) J. Ethnopharmacology 99, pp. 165-178.*
Khan et al. (2001) The Journal of Alternative and Complementary Medicine vol. 7, No. 5, pp. 405-515.*
Manyam, B.V. (1999) The Journal of Alternative and Complementary Medicine vol. 5, No. 1, pp. 81-88.*
Vinutha et al. (2007) J. Ethnopharmacology 109: 359-363.*
Bagchi et al. (2011) International Conference on Bioscience, Biochemistry and Bioinformatics IPCBEE vol. 5, 11-14.*
Joshi et al. (2006) J. Med. Food 9(1): 113-118.*
Mishra et al. (2008) Ann Indian Acad. Neurol. Jan.-Mar.: 11(1): 13-19.*
Rao et al. (2012) Alzheimer's Research and Therapy, 4: 22.*
Ringman et al. (2005) Curr. Alzheimer Res. 2(2): 131-136.*
Thusoo et al. (2014) BioMed Research International. vol. 2014, Article ID 614187, 4 pages.*
Rastogi, M., et al "Medicinal Plants and Alzheimer's Disease: an Overview," *Biomedicine, Indian Association of Biomedical Sciences* vol. 28, No. 2 (Apr. 1, 2008) pp. 73-80.
Aruna, A. et al: "Age related neurodegeneration with reference to Senile Dementia of Alzheimer's Type-Role of an Ayurvedic Formulation," *Journal of Neurochemistry*, vol. 109, No. Suppl. 1, (May 2009), p. 295, (Abstract).
Database WPI, Week 200673. Thomson Scientific, London, GB; AN 2006-699056 & IN MUM 200600505 A1 (MUNDEWADI A A) May 5, 2006. (Abstract).
Database WPI, Week 200781, Thomson Scientific, London, GB; AN 2007-876924 & IN DEL 200600212 A1 (S S T) Aug. 24, 2007(Abstract).
International Search Report and Written Opinion issued in PCT/IN2011/000236 dated Oct. 4, 2011.

* cited by examiner

*Primary Examiner* — Chris R Tate
*Assistant Examiner* — Russell Fiebig
(74) *Attorney, Agent, or Firm* — Venable LLP; Keith G. Haddaway

(57) ABSTRACT

According to this invention there is provided a herbal formulation for the prevention and management of neurodegenerative disorders comprising, hydro-methanolic extract of at least one plant selected from *Curcuma longa*, *Bacopa monnieri* and *Valeriana jatamansi*, at 70-80° C., maintaining the pH of the solution between 7-10, Separating the active compounds chromatographically and Subjecting the active compounds to the step of molecular characterization.

11 Claims, 12 Drawing Sheets

ROLE OF AN HERBAL FORMULATION IN THE PREVENTION AND MANAGEMENT OF AGE RELATED NEURODEGENERATIVE DISORDERS WITH SPECIAL REFERENCE TO SENILE DEMENTIA

FIELD OF INVENTION

This invention relates to role of an herbal formulation in the prevention and management of age related neurodegenerative disorders with special reference to Senile Dementia.

BACKGROUND OF INVENTION

Due to increase in life expectancy the number of aged are increasing throughout the world neurodegenerative disorders are the diseases of nervous system including brain, spinal cord and peripheral nerves. 10 percent of population over the age of 70 years has a significant memory loss out of which 50 percent cause is Alzheimer's diseases. The most common neurodegenerative disorders are Alzheimer's diseases (AD), Parkinson's disease (PD) and Huntington disease (HD). Protein aggregation oxidative stress, mitochondrial dysfunction and glutamate excito-toxicity are the biomarkers playing role in the process of neurodegeneration and death of neurons. Oxidative injury play a vital role in the degeneration and death of neurons. A number of reactive oxygen species (ROS) is found in the body with a wide variations in their site of formation, function and biological half life. An impaired uptake and increased accumulation of glucose and glutamate are found among AD and PD patients. It is reported that oxidative stress is not only related to protein aggregation rather is closely interrelated with mitochondrial dysfunction and glutamate excito-toxicity. The process of cell death also involves the excess release of inflammatory cytokines IL-6 and TNF-α. Thus a number of genetic and environmental factors play a role in the pathogenesis of neurodegeneration and neurodegenerative disorders. Senile dementia is characterized as loss of intellectual ability associated with old age like progressive deterioration in thinking, memory, behavior, personality and motor functions. Senile dementia is divided into two groups—
1. Dementia due to generalized atrophy (SDAT) and dementia due to vascular problems mainly due to strokes.
2. Depression, poor nutrition, drug poisoning, alcoholism, hyperglycemia, obesity, elevated homocystein etc., are the other causes of dementia.

In senile dementia the patient's brain function gradually deteriorates showing progressive loss of memory and mental ability with noticeable personality changes. Initially short term memory is affected—like affected person forgets what happened hours or minutes ago, feels difficulty in working routine work. Patient lose interest in various activities, he suffers from a kind of physical instability and possess aggression in his/her behavior and also exhibit moral inhibition. Recent conventional pharmacological strategies for the management of neurodegenerative disorders have shown decrease in progression of disease process rather than cure of disease, but the results are not very satisfactory and thus their application is restricted, particularly in reference to aging population.

Ayurveda has described several medicinal plants under the concept Medhya-rasayana which refers to the agents acting on higher brain function by interacting on ability or power of acquisition (intelligence), ability or power of retention and ability or power of recall of memory by amelioration of seven Medha of the individuals. In Ayurveda several medhya rasayana drugs are kept under category of medhya which are responsible for facilitating learning and memory. Taking lead from ancient literature the present study was conducted in various experimental and clinical trials.

OBJECTS OF INVENTION

The major object of present invention is to propose an Ayurvedic plant based formulation beneficial in the prevention and management of neurodegenerative disorders like senile dementia, vascular dementia and senile dementia of Alzheimer's type among aged population.

Another object of present invention is to propose a plant based Ayurvedic formulation effective in the prevention and management of memory and attention span among elderly people.

Still another object of present study is to proposed an Ayurvedic formulation beneficial to check the further loss of memory and cognition among aged.

Further, object of present invention is to propose a novel formulation beneficial in amelioration of neuro-chemical markers like acetylcholine, serotonin, nor-adrenaline, dopamine particularly glutamate involved in neurodegeneration.

Yet another object of present invention is to propose a plant based formulation showing effectivity on various oxidative stress markers like TBARS, glutathione, superoxide dismutase (SOD), Catalase and GPx.

One of the objects of present invention is to propose a novel Ayurvedic formulation beneficial in reducing the brain inflammation by acting on inflammatory cytokines IL-6, TNF-α including hs. C-reactive protein.

Still another object of present invention is to propose a plant based formulation beneficial in reducing the elevated homocysteine level among senile dementia subjects and others suffering from neurodegenerative disorders.

Further, another object of present invention is to propose a plant based Ayurvedic formulation effective in improving the orientation, working memory, language and communication skill among elderly people having neurodegeneration.

Another object of present invention is to propose an Ayurvedic formulation having beneficial role in improving the over all mental performance and also effective in maintenance of general health status among elderly population.

STATEMENT OF INVENTION

According to this invention there is provided a novel Ayurvedic formulation showing beneficial role in the prevention and management of neurodegenerative disorders like senile dementia, senile dementia of Alzheimer's type, vascular dementia caused due to stroke and neurodegeneration associated with various etiological factors like diabetes mellitus, obesity, hypertension, dyslipidemia etc.

Further, according to this invention there is provided a process for the preparation of novel Ayurvedic formulation as claimed in claim 1 comprising of preparing hydromethanolic extract of *Valeriana jatamansi* (Tagar, rhizome), *Bacopa monnieri* (Brahmi, whole plant) and *Curcuma longa* (Haridra, rhizome) by using water (aqueous) and methanol (30:70) at 70-80° C. and maintaining the pH of solution between 7-10, separating chromatographically the active compound by using TLC, HPLC, and HPTLC supporting the molecular characterization of plant extract by using IR and NMR.

DETAILED DESCRIPTION OF INVENTION

The hydro-methanolic extract of three Ayurvedic plants *Valeriana jatamansi*, *Curcuma longa* and *Bacopa monnieri* by using 30:70 ratio of water and methanol respectively is utilized for present study. The water utilized for extraction was decontaminated for any type of bacterial or abnormal growth by using reverse osmosis plant. After extraction the presence of active molecules in various plant extracts were identified by HPLC, HPTLC and NMR procedures.

The biological activity was studied on the basis of mode of action of single plant selected for combined formulation as well as combined formulation by assessing their role on various targets involved in neurodegeneration as well as neurodegenerative disorders. The bio-molecular reaction following the interaction between the chemical and biological markers like cholinergic, dopaminergic, glutamatergic system, oxidative stress markers, inflammatory cytokines and also the neuropyschological assessments were evaluated.

The pre-clinical toxicological studies of single as well as combined formulation were carried out to determine safety profile of present novel test formulation. The efficacy profile of test formulation were also done in pre-clinical animal model of Alzheimer's disease and age consistent status of various targets like neurotransmitters, neuro-inflammatory markers and oxidative stress markers. The mode of action of single plant candidate and combined formulation was determined in animal studies.

The beneficial role of test formulation on cholinergic, dopaminergic and glutamate excito-toxicity effect, anti-neuro-inflammatory activity and anti-oxidant activity was determined in various animal models before utilizing the test formulation for human consumption.

Extraction Procedure:

The dried rhizome of *Valeriana jatamansi*, dried rhizome of *Curcuma longa*, and dried whole plant of *Bacopa monnieri*, were utilized for extraction. The hydro-methanolic extract of the plants were utilized for the identification of active compound present in the plants. After extraction, the extracted parts were taken for chromatographic separation by using TLC, HPLC, and HPTLC. After identification and separation of active compound, the molecular characterization was carried out by using IR and NMR.

Figure 1:
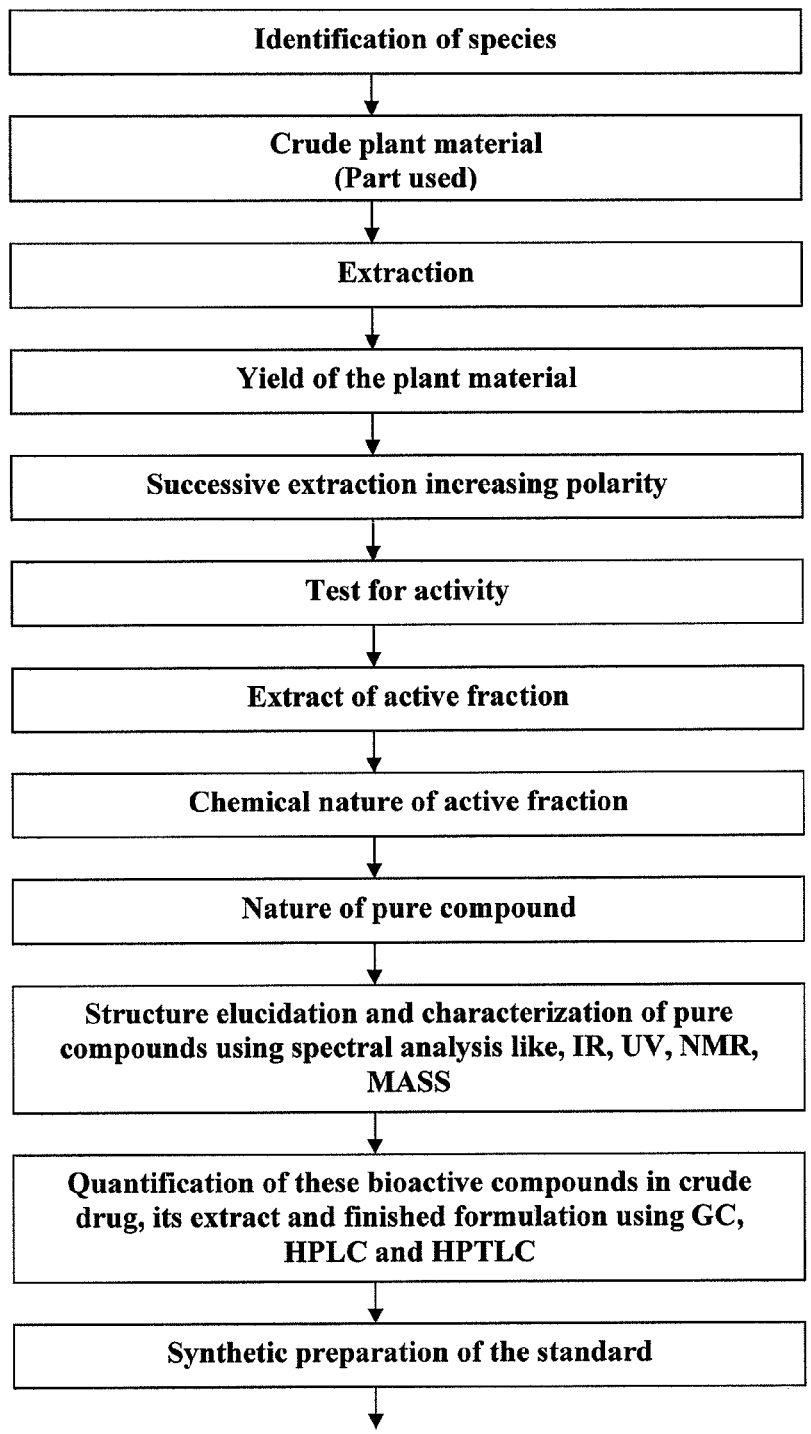
FIG. 1 is a flow diagram of the process.
Figure 1:
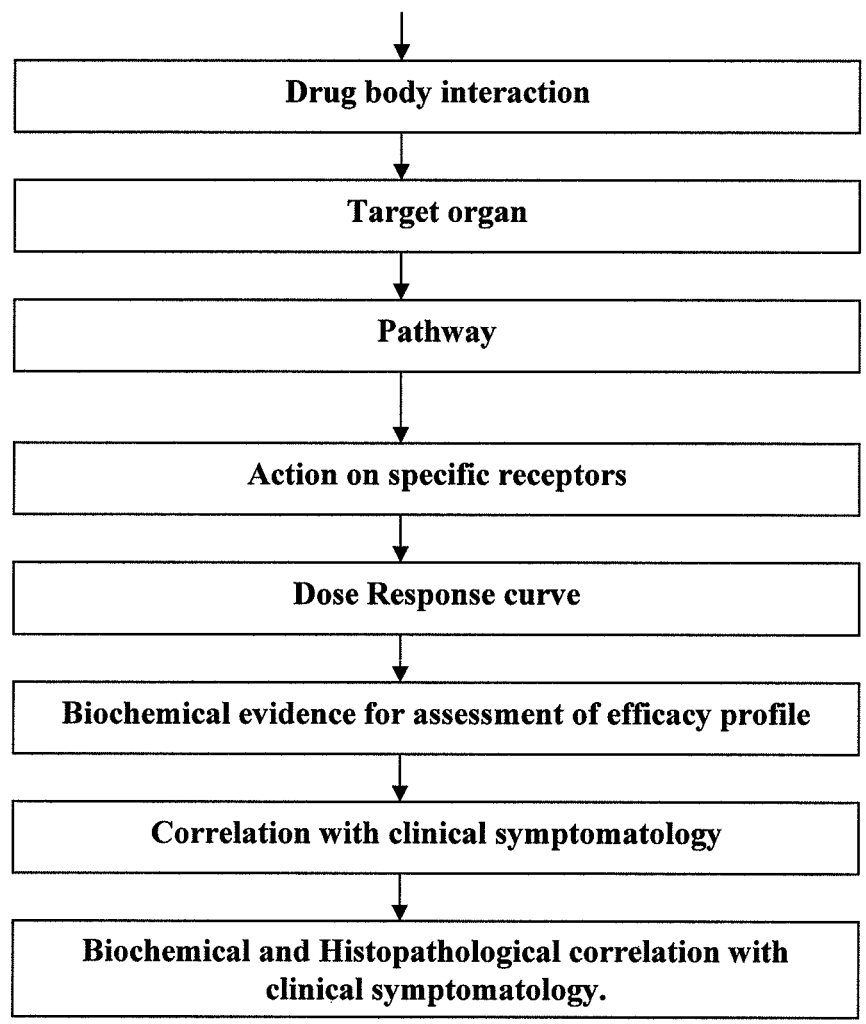

The extraction was done at the temperature of 70-80° C. The pH of the solution was maintained between 7-10. The steps carried out to isolate the active compound to assess the activity of test formulation are shown in FIG. 1.

According to this invention, there is provided an Ayurvedic formulation for the prevention and management of neurodegenerative disorders particularly for senile dementia and senile dementia of Alzheimer's type. The present test formulation comprising of the following ingredients:

|   | Name of the Plants | Parts used |
|---|---|---|
| 1. | *Curcuma longa* (Haridra) | rhizome |
| 2. | *Valeriana jatamansi* (Tagar) | rhizome |
| 3. | *Bacopa monnieri* (Brahmi) | whole plant |

Preferably, the aforesaid plants are present in the formulation in the following doses—

|   | Name of the Plants | Dose range |
|---|---|---|
| 1. | *Curcuma longa* | 150-400 mg/day |
| 2. | *Valeriana jatamansi* | 200-450 mg/day |
| 3. | *Bacopa monnieri* | 250-500 mg/day |

The formulation also comprise known additive such as minerals, vitamins, salts filler (for capsulation or to prepare syrup) and binders, if required to present in trace amount.

Thus any known additive or supplement is added to prepare the final formulation as required and present in trace amount. Reference is made here in capsule form (500 mg each). However, it would be apparent that the preparation may also be in the form of syrup/tablet.

Preferably but without implying any limitation the preparation comprises—

|   | Name of the plant | Dose |
|---|---|---|
| 1. | *Curcuma langa* | 250 mg/day |
| 2. | *Valeriana jatamansi* | 325 mg/day |
| 3. | *Bacopa monnieri* | 375 mg/day |

Hypothesis:

The present test formulation is based on the combined effect of three Ayurvedic plant extract namely *Curcuma longa*, *Valeriana jatamansi* and *Bacopa monnieri*. This formulation has been proven for its neuro-chemical, neuro-modulatory, anti-inflammatory and anti-oxidant activity and the most important potential role is for memory and attention span enhancing activity among aged people. These effects are mainly mediated through its glutamate inhibitory activity as well as amelioration of cholinergic and dopaminergic neurons. Further, the novel formulation prepared by using specific doses of three plant extracts have exerted anti-oxidant role by regulation of oxidative enzymes.

A number of changes take place in the brain during neurodegeneration or aging at molecular, cellular, structural and functional level. Neurotransmitters such as acetylcholine glutamate, dopamine play an important role in the regulation of neuronal circuits and influence the neurodegenerative process. Glutamate and GABA, the major excitatory and inhibitory neurotransmitters are responsible for the protection of neuronal survival and synaptic plasticity.

Decrease 5-HT receptors were found in dementia. Serotonergic neurons either inhibits or increase the release of dopamine concentration, thus influence dementia directly. GABA is the primary inhibitory neurotransmitter in the CNS and abnormality is significantly associated with behavioral changes in neurodegenerative disorders. Regulation of 5-HT results in the regulation of aggression, mood, feeding, sleep, temperature, motor activity etc.

Decrease in cholinergic markers cholin-acetyl-transferase (AchE) in the cortex, loss of neurons in nucleus basalis of meynert and also reduction in muscarinic type-II pre-synaptic receptor density are estimated in various type of dementia. It is reported that *Valeriana jatamansi* is a potent nervine tonic and has sedative effects thus it produces mental relaxation and induces sleep.

As vascular inflammation is significantly involved with neurodegenerative disorders, high level of Interleukins, Tumor Necrosis Factor are responsible for neuro-inflammation. Further, high sensitive C-reactive protein is an important neuro-inflammatory factor manifesting vascular inflammation in the brain, particularly in Alzheimer's disease and Parkinson's disease. Oxidative injury plays a major role in the death and degeneration of neurons and also contributes in platelet aggregation and mitochondrial dysfunction and glutamate excitotoxicity. Recently various studies have suggested that apoptosis rather than necrosis is primarily responsible for loss of neurons and that caspases are the major executioners of apoptosis in common neurodegenerative diseases. This mechanism is important when studied in relation to aging brain. A number of acetylcholine esterase inhibitors, MAO-B inhibitors chelaters etc are being used for their multi-targeted action that prevents loss of mitochondrial permeability, cytochrome C release and down regulated the expression of pro-apoptonic genes, but the application of such agents are restricted due to unsatisfactory results and side effects.

Keeping the above facts in view and effective role of plants that acted on various targets involved with neurodegenerative process determined in pre-clinical models, it was thought to propose a better remedial measure for the prevention and management of neurodegenerative process as well as neurodegenerative disorders particularly Senile Dementia, SDAT and vascular dementia caused due to stroke.

About the Plant:

*Curcuma longa*: It belongs to Zingiberaceae family and found all over India in abundance. The active constituents of *curcuma longa* are flavonoid, curcumin and volatile oils including timerone, atlantone and zingiberone. It has antioxidant, hepato-protective, anti-oxidant and potent anti-inflammatory activity. It improves cognitive deficit and prevents amyloidal accumulation

*Bacopa monnieri*: *Bacopa monnieri* is one of the major ingredients of present test formulation that belongs to family scrophulariaceae. It has shown potential role in improving mental ability, intelligence, concentration and memory performance. It is a potent nervine tonic. It is reported that *Bacopa monnieri* crosses the blood brain barrier, regulates the cholinergic neuron, prevents the further loss of acetylcholine and thus is effective in the prevention and management of neurodegenerative disorders. It has also shown anti-oxidant role.

*Valeriana Jatamansi* belongs to family Valerianceae also known as jatamansi. Rhizome is used medicinally. This species is globally distributed at altitude range of 1500-3600 m. Valerian, active compound of V-Jatamansi has been shown to improve sleep quality and reduce blood pressure.

The rhizome of *Valeriana Jatamansi* is antispasmodic, carminative, diuretic, hypnotic, powerfully nervine, sedative and stimulant. It is also used in the treatment of painful menstruation, cramps, hypertension and irritable bowel syndrome.

Example-I

When the hydro-methanolic extract of *Bacopa monnieri* (40 mg/kg) and *Curcuma longa* (20 mg/kg) mixed and orally administered to experimental animals it restored the level of acetylcholine, dopamine, 5-HT and nor-adrenaline in aged mice brain where as it reduced the elevated glutamate content in the same experimental model. The drug also revealed reduction in inflammatory markers as well as the anti-oxidant activity in aged brain.

Example-II

When the hydro-methanolic extract of *Bacopa monnieri* (35 mg/kg), *Curcuma longa* (20 mg/kg) and *Valeriana jatamansi* (25 mg/kg) mixed and given to streptozotocin neurotoxin induced Alzheimer's disease model rats a significant elevation in acetylcholine, ChAt activity, serotonergic, nor-adrenaline concentration were estimated in drug treated group. The rats exerted better learning ability following test formulation treatment.

Example-III

In clinical trial when the hydro-methanolic extract of *Valeriana jatamansi* (350 mg/day) and *Bacopa monnieri* (450 mg/day) mixed and prescribed for oral administration to diagnosed senile dementia cases improvement in short and long term memory, attention span and reduction in anxiety and depression scores were noticed.

Example-IV

The organic extract of *Bacopa monnieri* (425 mg/day) and *Curcuma longa* (400 mg/day) mixed and given orally to senile dementia cases a significant anti-oxidant role was observed as glutathione level increased and lipid peroxidase levels decreased following test formulation treatment.

Example-V

The organic extract of *Curcuma longa* (425 mg/day) and *Valeriana jatamansi* (450 mg/day) mixed and prescribed for oral administration in two divided doses exerted significant reduction in inflammatory cytokines IL-6, and TNF-α indicating improvement in neurodegenerative process. CRP also reduced in test drug treatment group suggesting improved vascular inflammation.

Example-VI

When the organic extract of *Bacopa monnieri* (425 mg/day) and *Valeriana jatamansi* (425 mg/day) mixed and given to diagnosed cases of Senile Dementia of Alzheimer's Type improvement in clinical symptoms like aggression, sleep disturbance, communication difficulties, psychotic feature (hallucination and delusion) was observed.

Example-VII

When the hydro-methanolic extract of *Curcuma longa* (375 mg/day), *Bacopa monnieri* (450 mg/day) mixed and given to SDAT cases elevation in 5-HT, nor-adrenaline and dopamine level was noticed. A decrease in glutamate level was also estimated.

Example-VIII

When the organic extract of *Valeriana jatamansi* 450 mg/day and *Bacopa monnieri* 425 mg/day mixed and given to SDAT cases improvement in sleep pattern, behavioral abnormalities were recorded after 3-6 months treatment.

Example-IX

The most beneficial and promising results were noticed when the hydro-methanolic extract of *Bacopa monnieri* in the dose of 375 mg/day, *Valeriana jatamansi* in the dose of 325 mg/day and *Curcuma longa* 250 mg/day mixed and given to neurodegenerative disorder patients both senile dementia and SDAT cases. An improvement in Mini Mental Scores, memory span, attention span was recorded and no further decline is reported. Further, an elevation in 5-HT, nor-adrenaline levels were estimated. The test drug exerted reduction in inflammatory bio-markers IL-6 and TNF-α. The test drug has shown overall improvement in mental health status by improving memory and cognition and also general feeling of well being among senile dementia, SDAT and other neurodegenerative disorders. The test formulation has anti-oxidant, anti-inflammatory and neuromodulatory activity. The drug is safe and can be given for longer time.

Experimental Evidence:

Study-I

TABLE 1

Age consistent status of neurotransmitter and beneficial role of test formulation

| Groups | Acetylcholine (nm/gm) | Dopamine (µg/gm) | Nor-adrenaline (µg/gm) | 5-HT (µg/gm) | Glutamate (µmol/gm wt. tissue) |
|---|---|---|---|---|---|
| Group-I * (4 months old mice) | 26.82 ± 3.88 | 0.42 ± 0.08 | 0.45 ± 0.16 | 0.67 ± 0.09 | 10.73 ± 2.15 |
| Group-II ** (10 months old mice) | 16.82 ± 2.81 | 0.31 ± 0.09 | 0.19 ± 0.07 | 0.44 ± 0.08 | 16.83 ± 3.41 |
| Group-III *** (10 months old mice + test drug) | 23.59 ± 2.93 | 0.39 ± 0.25 | 0.38 ± 0.25 | 0.59 ± 0.05 | 14.09 ± 2.45 |
| Comp. | | | | | |
| * vs ** | P < 0.01 | P < 0.05 | P > 0.05 | P < 0.05 | P < 0.05 |
| ** vs *** | P < 0.01 | P > 0.05 | P > 0.05 | P > 0.05 | P > 0.05 |

TABLE 2

Age consistent oxidative injury and benefits of novel Ayurveda formulation on oxidative stress markers

| Groups | TBARS (nm/mg protein) | Glutathione (µg/mg protein) | SOD (IU/mg protein) | Catalase (µM H2O2 oxidized/ min/mg protein) | GPx (µM glutathione oxidized/ min/mg protein) |
|---|---|---|---|---|---|
| Group-I * (4 months old mice) | 0.297 ± 0.042 | 4.251 ± 1.085 | 47.994 ± 9.310 | 17.091 ± 2.954 | 3.194 ± 0.982 |
| Group-II ** (10 months old mice) | 0.578 ± 0.039 | 2.649 ± 0.102 | 28.773 ± 5.901 | 11.801 ± 1.013 | 2.045 ± 0.172 |
| Group-III *** (10 months old mice + test drug) | 0.429 ± 0.033 | 3.287 ± 0.350 | 36.801 ± 4.612 | 14.914 ± 2.876 | 2.985 ± 0.103 |
| Comp: | | | | | |
| * vs ** | P < 0.001 | P > 0.05 | P > 0.05 | P > 0.05 | P > 0.05 |
| ** vs *** | P < 0.05 | P > 0.05 | P > 0.05 | P > 0.05 | P > 0.05 |

TABLE 3

Age consistent elevation in inflammatory cytokines, homocysteine and beneficial role of novel formulation.

| Groups | IL-6 (pg/ml) | hs CRP (mg/L) | TNF-α (pg/ml) | Homocysteine (mmol/L) |
|---|---|---|---|---|
| Group-I * (4 months old mice) | 111.0 ± 12.15 | 4.87 ± 0.85 | 342.8 ± 15.26 | 7.93 ± 1.05 |
| Group-II ** (10 months old mice) | 302.0 ± 8.53 | 7.99 ± 0.93 | 604.85 ± 12.96 | 13.81 ± 1.63 |

TABLE 3-continued

Age consistent elevation in inflammatory cytokines, homocysteine and beneficial role of novel formulation.

| Groups | IL-6 (pg/ml) | hs CRP (mg/L) | TNF-α (pg/ml) | Homocysteine (mmol/L) |
|---|---|---|---|---|
| Group-III *** (10 months old mice + test drug) | 187.0 ± 9.86 | 5.69 ± 0.95 | 481.21 ± 18.78 | 9.85 ± 0.98 |
| Comp | | | | |
| * vs ** | $P < 0.001$ | $P > 0.05$ | $P < 0.001$ | $P < 0.001$ |
| ** vs *** | $P < 0.001$ | $P > 0.05$ | $P > 0.05$ | $P < 0.01$ |

Study-II

TABLE 1

Changes in Ach concentration following test formulation

| | Acetylcholine concentration (n mol/gm.) | | | |
|---|---|---|---|---|
| | Frontal cortex | | Hippocampus | |
| Treated groups | Day 14 | Day 21 | Day 14 | Day 21 |
| Vehicle (ACSF) * | 22.84 ± 3.45 | 26.92 ± 5.06 | 30.44 ± 4.98 | 28.94 ± 3.75 |
| Td. with STZ ** | 11.84 ± 2.11 | 6.92 ± 1.82 | 15.87 ± 2.65 | 12.99 ± 2.87 |
| Td. with test drug *** | 24.94 ± 3.45 | 26.22 ± 4.04 | 29.84 ± 3.11 | 31.75 ± 4.14 |
| Td. with STZ + test drug **** | 17.87 ± 2.85 | 16.92 ± 3.01 | 23.97 ± 3.75 | 22.20 ± 2.97 |
| Comp. | | | | |
| * vs ** | $p < 0.001$ | $p < 0.001$ | $p < 0.001$ | $p < 0.001$ |
| ** vs *** | $p < 0.001$ | $p < 0.001$ | $p < 0.001$ | $p < 0.001$ |
| *** vs **** | $p < 0.001$ | $p < 0.01$ | $p < 0.01$ | $p < 0.01$ |

TABLE 2

Effect of test formulation on ChAT activity

| | ChAT activity (n mol/mg protein/hour) | | | |
|---|---|---|---|---|
| | Frontal cortex | | Hippocampus | |
| Treated groups | Day 14 | Day 21 | Day 14 | Day 21 |
| Vehicle (ACSF) * | 21.84 ± 3.01 | 23.97 ± 4.11 | 22.05 ± 2.92 | 19.85 ± 2.82 |
| Td. with STZ ** | 13.82 ± 2.02 | 10.75 ± 1.68 | 8.92 ± 1.72 | 6.08 ± 1.01 |
| Td. with test drug *** | 20.85 ± 3.12 | 22.70 ± 2.91 | 18.22 ± 2.75 | 19.75 ± 2.10 |
| Td. with STZ + test drug **** | 15.58 ± 2.33 | 16.93 ± 3.11 | 14.88 ± 3.14 | 13.87 ± 2.91 |
| Comp | | | | |
| * vs ** | $p < 0.001$ | $p < 0.001$ | $p < 0.001$ | $p < 0.001$ |
| ** vs *** | $p < 0.001$ | $p < 0.001$ | $p < 0.001$ | $p < 0.001$ |
| *** vs **** | $p < 0.01$ | $p < 0.05$ | $p < 0.05$ | $p < 0.01$ |

TABLE 3

Effect of test formulation on Nor-adrenaline level

| | Nor-adrenaline (μ gm/gm tissue) | | | |
|---|---|---|---|---|
| | Frontal cortex | | Hippocampus | |
| Treated groups | Day 14 | Day 21 | Day 14 | Day 21 |
| Vehicle (ACSF) * | 0.264 ± 0.032 | 0.271 ± 0.041 | 0.262 ± 0.050 | 0.265 ± 0.036 |
| Td. with STZ ** | 0.123 ± 0.022 | 0.106 ± 0.028 | 0.148 ± 0.031 | 0.102 ± 0.026 |
| Td. with test drug *** | 0.271 ± 0.048 | 0.284 ± 0.038 | 0.275 ± 0.037 | 0.288 ± 0.041 |
| Td. with STZ + test drug **** | 0.152 ± 0.030 | 0.164 ± 0.034 | 0.150 ± 0.036 | 0.162 ± 0.028 |
| Comp | | | | |
| * vs ** | $p < 0.05$ | $p < 0.01$ | $p > 0.05$ | $p < 0.05$ |
| ** vs *** | $p < 0.001$ | $p < 0.05$ | $p > 0.05$ | $p > 0.05$ |
| *** vs **** | $p < 0.05$ | $p < 0.01$ | $p < 0.05$ | $p < 0.001$ |

TABLE 4

Effect of test formulation on Serotonin level

| | Serotonin (μ gm/gm tissue) | | | |
|---|---|---|---|---|
| | Frontal cortex | | Hippocampus | |
| Treated groups | Day 14 | Day 21 | Day 14 | Day 21 |
| Vehicle (ACSF) * | 0.432 ± 0.036 | 0.442 ± 0.020 | 0.315 ± 0.024 | 0.327 ± 0.021 |
| Td. with STZ ** | 0.289 ± 0.011 | 0.221 ± 0.014 | 0.240 ± 0.017 | 0.210 ± 0.015 |
| Td. with test drug *** | 0.489 ± 0.032 | 0.479 ± 0.027 | 0.392 ± 0.036 | 0.385 ± 0.030 |
| Td. with STZ + test drug **** | 0.354 ± 0.021 | 0.362 ± 0.024 | 0.288 ± 0.022 | 0.268 ± 0.019 |
| Comp | | | | |
| * vs ** | $p < 0.05$ | $p < 0.01$ | $p > 0.05$ | $p < 0.05$ |
| ** vs *** | $p < 0.001$ | $p < 0.05$ | $p > 0.05$ | $p > 0.05$ |
| *** vs **** | $p < 0.05$ | $p < 0.01$ | $p < 0.05$ | $p < 0.001$ |

TABLE 5

Effect of test drug on Retention of active avoidance learning (RAAL)

| | RAAL (no. of trials) | |
|---|---|---|
| Treated group | Day 14 | Day 21 |
| Vehicle (ACSF) * | 7.11 ± 1.02 | 6.82 ± 1.06 |
| Td. with STZ ** | 13.03 ± 2.13 | 15.16 ± 2.12 |
| Td. with test drug *** | 6.58 ± 1.04 | 5.21 ± 0.92 |
| Td. with STZ + test drug **** | 10.31 ± 1.30 | 8.94 ± 1.04 |
| Comp | | |
| * vs ** | $p < 0.001$ | $p < 0.001$ |
| ** vs *** | $p < 0.001$ | $p < 0.001$ |
| *** vs **** | $p < 0.001$ | $p < 0.001$ |

Clinical Evidence

TABLE 1

Effect of test drug on clinical complaints in SDAT cases

| | | Complaints (In percent) | | | | | | | | |
|---|---|---|---|---|---|---|---|---|---|---|
| | | Aggression | | Sleep disturbance | | Communication difficulties | | Depression | | Psychotic features | |
| Treated groups | | BT | AT | BT | AT | BT | AT | BT | AT | BT | AT |
| Normal aged | P td (N = 62) | 24 38.70 | 24 38.70x | 9 14.51 | 10 16.12x | — — | — — | 16 25.80 | 17 27.41x | 6 9.67 | 9 14.51x |
| | T td (N = 68) | 25 36.76 | 59 86.76✿ | 22 32.35 | 64 94.11✿ | — — | — — | 15 22.05 | 58 85.29Ψ | 9 13.23 | 52 76.47✿ |
| SDAT cases | Pl td (N = 71) | 68 95.77 | 70 98.59* | 65 91.54 | 68 95.77* | 69 97.18 | 70 98.59* | 67 94.36 | 66 92.95* | 61 85.91 | 68 95.77* |
| | T td (N = 78) | 65 83.33 | 69 88.46# | 67 85.89 | 66 84.61# | 72 92.30 | 70 89.74# | 70 89.74 | 68 87.17# | 69 88.46 | 70 89.74# |

(BT = Before therapy; AT = After 6 months therapy)
Normal aged (Placebo treated) ATx = No improvement in percent;

Normal aged (Test drug treated) AT✿ = Improvement in percent
SDAT (Placebo treated) AT* = No improvement in percent;
SDAT (Test drug treated) AT# = Improvement in percent

TABLE 2

Effect of test drug on mini mental state examination in SDAT cases

| | | Mini-mental state examination (Score) | | | Comp. initial vs 6 months treatment |
|---|---|---|---|---|---|
| Treated groups | | Initial | After 3 months | After 6 months | |
| Normal aged | P td (N = 62) | 18.75 ± 2.90 | 18.62 ± 3.01 | 17.82 ± 2.71 | $P > 0.05$ |
| | TD td (N = 68) | 18.89 ± 3.01 | 19.83 ± 2.77 | 20.42 ± 3.04 | $P < 0.01$ |

TABLE 2-continued

Effect of test drug on mini mental state examination in SDAT cases

| Treated groups | | Mini-mental state examination (Score) | | | Comp. initial vs 6 months treatment |
|---|---|---|---|---|---|
| | | Initial | After 3 months | After 6 months | |
| SDAT cases | P td (N = 71) | 10.45 ± 1.34 | 9.23 ± 2.02 | 8.25 ± 1.01 | P < 0.001 |
| | T td (N = 78) | 11.02 ± 1.66 | 11.68 ± 2.05 | 12.29 ± 2.26 | P < 0.001 |

Figure 2:
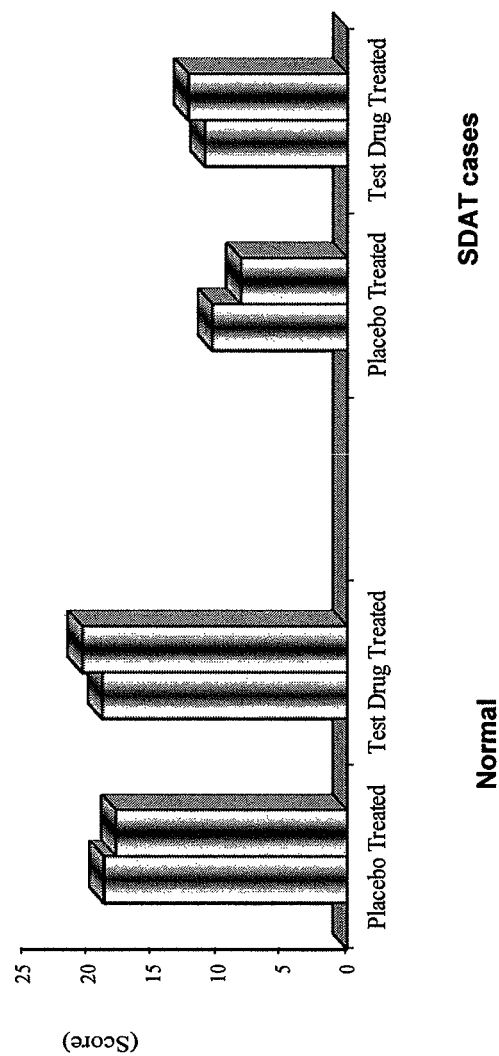
FIG. 2 is showing the effect of test drug on mini mental state examination in SDAT cases.

Results of the effect of test drug on mini mental state examination in SDAT cases are shown in FIG. 2.

TABLE 3

Effect of test drug on mini mental state examination and attention span in SDAT cases

| Treated groups | | Attention Span (Score) | | | Comp. initial vs 6 months treatment |
|---|---|---|---|---|---|
| | | Initial | After 3 months | After 6 months | |
| Normal aged | P td (N = 62) | 10.65 ± 2.82 | 10.42 ± 3.11 | 9.87 ± 2.13 | P > 0.05 |
| | T td (N = 68) | 11.26 ± 2.17 | 11.10 ± 2.03 | 10.36 ± 1.93 | P < 0.05 |
| SDAT cases | P td (N = 71) | 4.98 ± 1.21 | 4.11 ± 0.97 | 3.72 ± 0.75 | P < 0.001 |
| | T td (N = 78) | 5.12 ± 1.05 | 5.83 ± 0.92 | 6.08 ± 1.23 | P < 0.001 |

Figure 3:
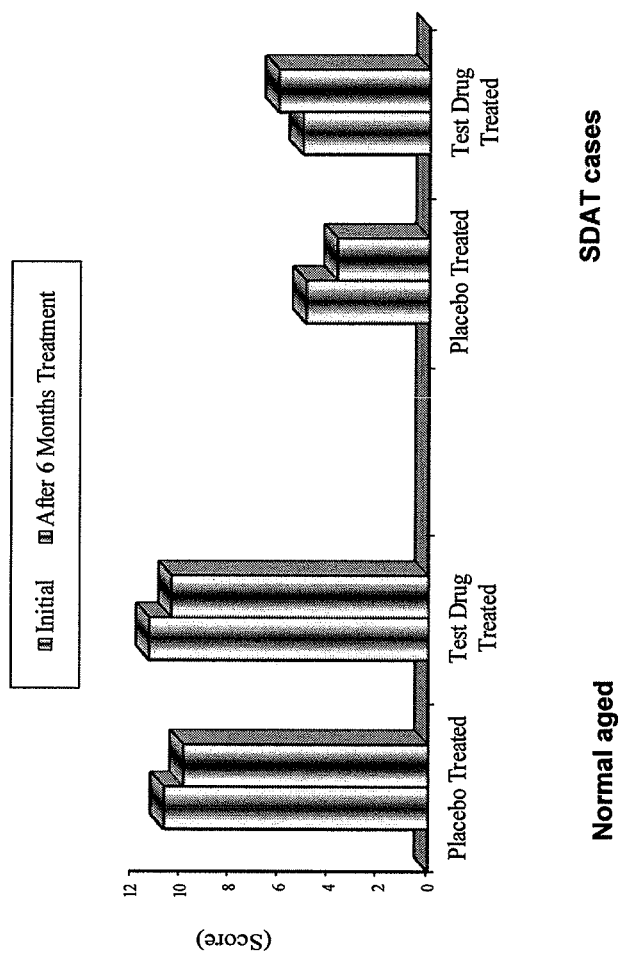
FIG. 3 is showing the effect of test drug on mini mental state examination and attention span in SDAT cases.

Results of the effect of test drug on mini mental state examination and attention span in SDAT cases are shown in FIG. 3.

TABLE 4

Effect of test drug on short term memory in SDAT cases

| Treated groups | | Short term memory (Score) | | | Comp. initial vs 6 months treatment |
|---|---|---|---|---|---|
| | | Initial | After 3 months | After 6 months | |
| Normal aged | P td (N = 62) | 7.82 ± 2.13 | 7.73 ± 1.90 | 7.65 ± 1.75 | P > 0.05 |
| | T td (N = 68) | 8.04 ± 1.55 | 8.93 ± 1.81 | 9.63 ± 2.12 | P < 0.001 |
| SDAT cases | P td (N = 71) | 3.81 ± 0.97 | 3.26 ± 1.02 | 2.84 ± 0.85 | P < 0.001 |
| | T td (N = 78) | 3.24 ± 0.77 | 3.88 ± 0.93 | 4.23 ± 1.04 | P < 0.001 |

Figure 4:
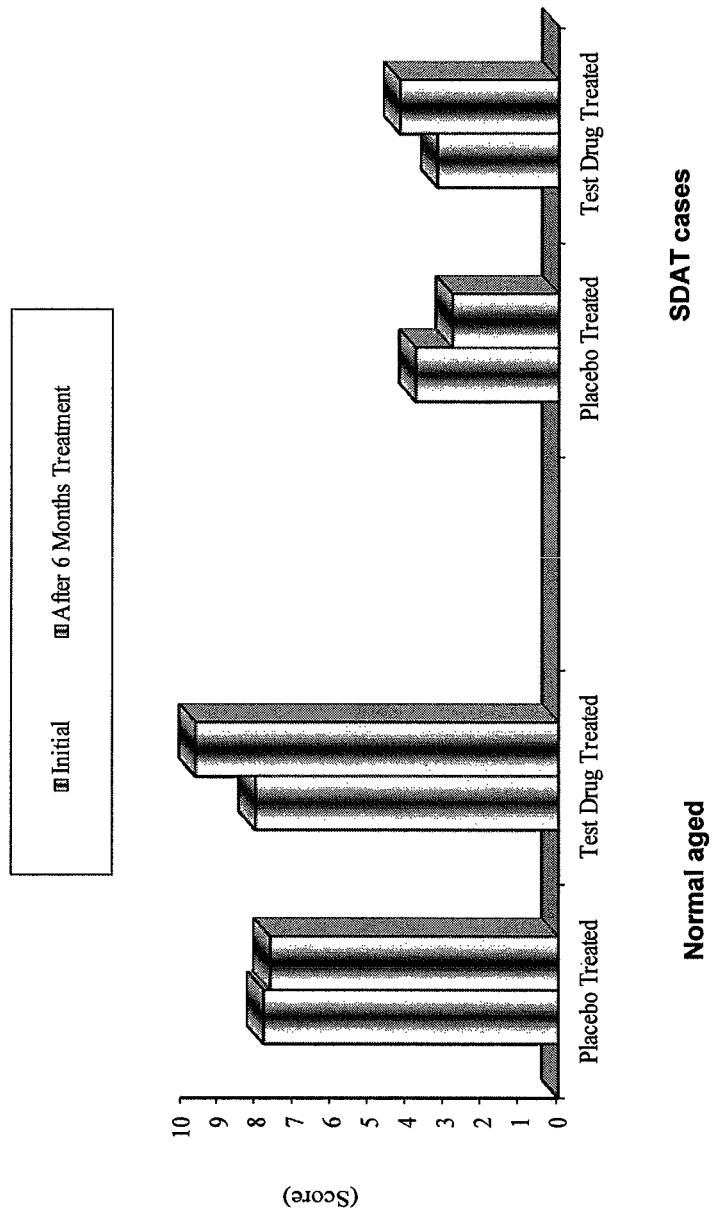
FIG. 4 is showing the effect of test drug on short term memory in SDAT cases.

Results of the effect of test drug on short term memory in SDAT cases are shown in FIG. 4.

TABLE 5

Effect of test drug on long term memory in SDAT cases

| Treated groups | | Long term memory (Score) | | | Comp. initial vs 6 months treatment |
|---|---|---|---|---|---|
| | | Initial | After 3 months | After 6 months | |
| Normal aged | P td (N = 62) | 6.13 ± 2.12 | 6.05 ± 1.75 | 5.48 ± 0.98 | P < 0.05 |
| | T td (N = 68) | 5.85 ± 1.35 | 6.75 ± 1.22 | 6.90 ± 2.01 | P < 0.01 |
| SDAT cases | P td (N = 71) | 1.75 ± 0.61 | 1.66 ± 0.25 | 1.52 ± 0.55 | P < 0.05 |
| | T td (N = 78) | 1.68 ± 0.69 | 1.90 ± 0.52 | 2.23 ± 0.85 | P < 0.001 |

Figure 5:
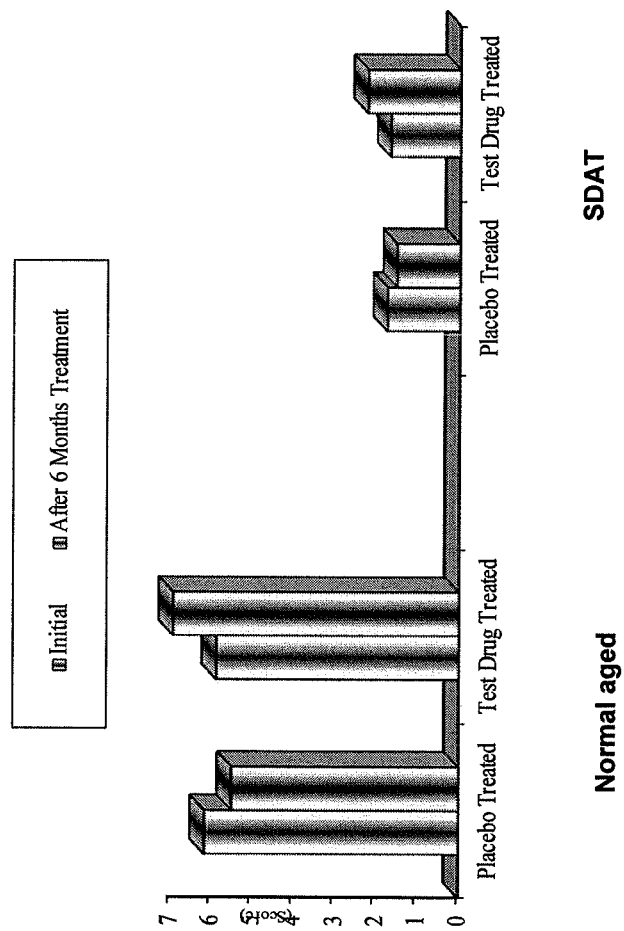
FIG. 5 is showing the effect of test drug on long term memory in SDAT cases.

Results of the effect of test drug on long term memory in SDAT cases are shown in FIG. 5.

TABLE 6

Effect of test drug on Anxiety level in SDAT cases

| Treated groups | | Anxiety Level (Score) | | | Comp. initial vs 6 months treatment |
|---|---|---|---|---|---|
| | | Initial | After 3 months | After 6 months | |
| Normal aged | P td (N = 62) | 53.90 ± 4.11 | 55.82 ± 3.92 | 54.77 ± 5.01 | P > 0.05 |
| | T td (N = 68) | 54.09 ± 3.11 | 52.75 ± 4.92 | 51.23 ± 3.75 | P < 0.05 |
| SDAT cases | P td (N = 71) | 65.14 ± 4.35 | 64.90 ± 6.39 | 66.82 ± 4.22 | P < 0.01 |
| | T td (N = 78) | 66.20 ± 5.16 | 64.81 ± 3.75 | 61.90 ± 6.08 | P < 0.001 |

Figure 6:
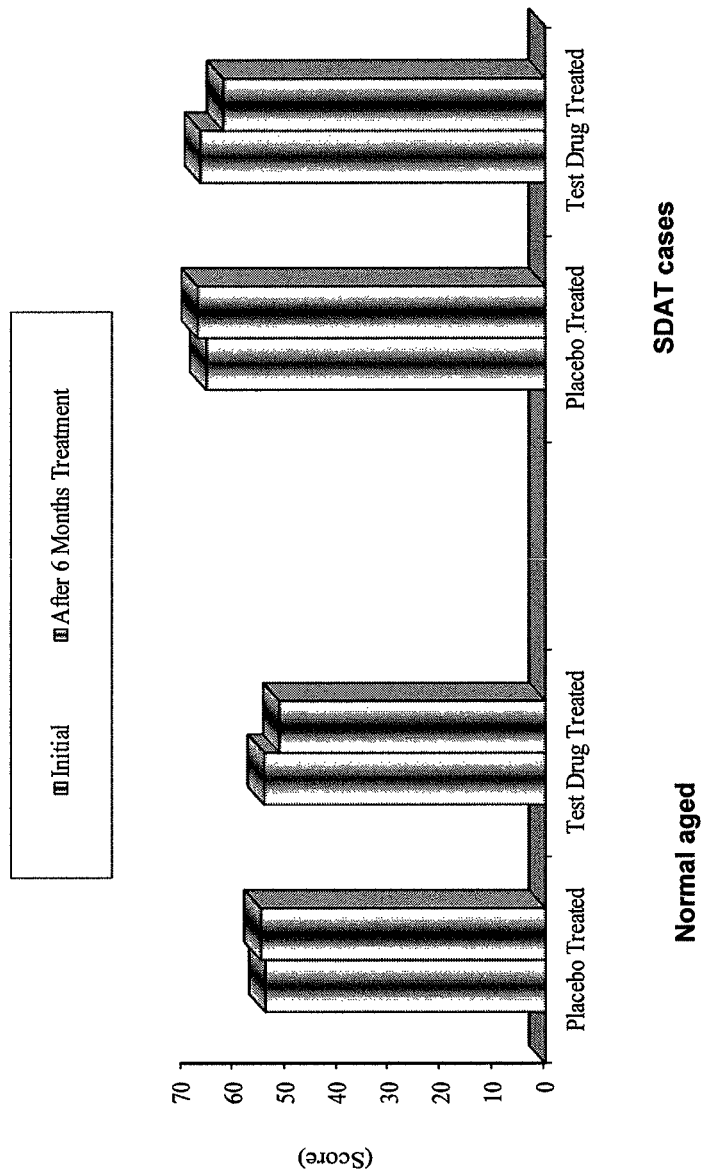
FIG. 6 is showing the effect of test drug on Anxiety level in SDAT cases.

Results of the effect of test drug on Anxiety level in SDAT cases are shown in FIG. 6.

TABLE 7

Effect of test drug on depression level in SDAT cases

| Treated groups | | Depression Level (Score) | | | Comp. initial vs 6 months treatment |
|---|---|---|---|---|---|
| | | Initial | After 3 months | After 6 months | |
| Normal aged | P td (N = 62) | 10.27 ± 3.04 | 11.08 ± 2.45 | 11.62 ± 2.14 | P < 0.01 |
| | T td (N = 68) | 9.72 ± 2.46 | 8.20 ± 1.71 | 7.98 ± 2.85 | P < 0.001 |
| SDAT cases | P td (N = 71) | 15.27 ± 2.45 | 15.98 ± 3.17 | 17.60 ± 2.13 | P < 0.001 |
| | T td (N = 78) | 16.23 ± 3.10 | 14.38 ± 2.99 | 13.62 ± 4.02 | P < 0.001 |

Figure 7:
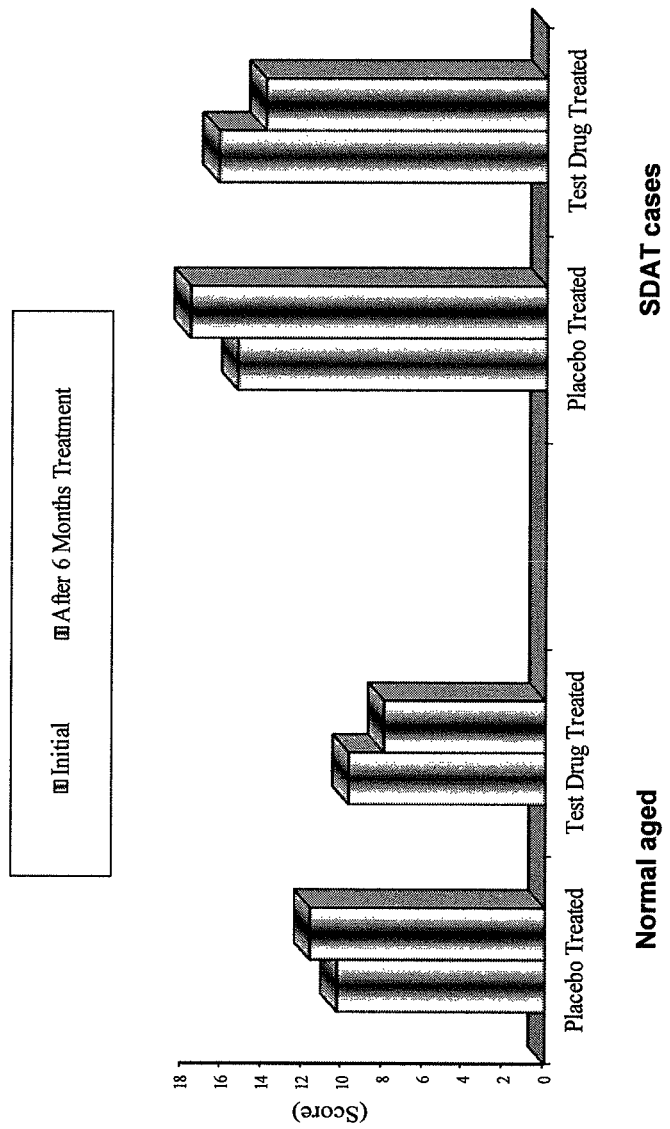
FIG. 7 is showing the effect of test drug on depression level in SDAT cases.

Results of the effect of test drug on depression level in SDAT cases are shown in FIG. 7.

TABLE 8

Effect of test drug on hs C-Reactive Protein level in SDAT cases

| Treated groups | | CRP (mg/L) | | | Comp. initial vs 6 months treatment |
|---|---|---|---|---|---|
| | | Initial | After 3 months | After 6 months | |
| Normal aged | P td (N = 62) | 2.10 ± 0.48 | 1.97 ± 0.45 | 2.28 ± 0.70 | P < 0.05 |
| | T td (N = 68) | 2.38 ± 0.76 | 1.85 ± 0.36 | 1.54 ± 0.84 | P < 0.001 |
| SDAT cases | P td (N = 71) | 6.23 ± 1.09 | 5.98 ± 0.88 | 6.04 ± 1.12 | P > 0.05 |
| | T td (N = 78) | 7.11 ± 1.02 | 6.25 ± 0.97 | 5.62 ± 1.23 | P < 0.001 |

Figure 8:
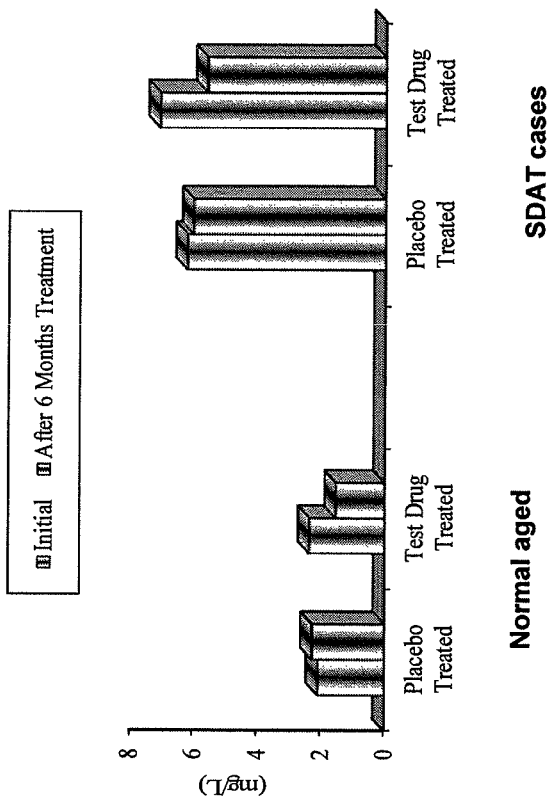
FIG. 8 is showing the effect of test drug on hs C-Reactive Protein level in SDAT cases.

Results of the effect of test drug on hs C-Reactive Protein level in SDAT cases are shown in FIG. 8.

TABLE 9

Effect of test drug on Interleukin-6 level in SDAT cases

| Treated groups | | Interleukin-6 (pg/ml) | | | Comp. initial vs 6 months treatment |
|---|---|---|---|---|---|
| | | Initial | After 3 months | After 6 months | |
| Normal aged | P td (N = 62) | 2.28 ± 0.41 | 2.19 ± 0.28 | 2.55 ± 0.24 | P < 0.001 |
| | T td (N = 68) | 2.23 ± 0.24 | 1.68 ± 0.33 | 1.35 ± 0.20 | P < 0.001 |

TABLE 9-continued

Effect of test drug on Interleukin-6 level in SDAT cases

| Treated groups | | Interleukin-6 (pg/ml) | | | Comp. initial vs 6 months treatment |
|---|---|---|---|---|---|
| | | Initial | After 3 months | After 6 months | |
| SDAT cases | P td (N = 71) | 3.48 ± 0.37 | 3.98 ± 0.35 | 4.68 ± 1.02 | P < 0.001 |
| | T td (N = 78) | 4.12 ± 1.06 | 3.68 ± 0.91 | 3.15 ± 0.68 | P < 0.001 |

Figure 9:
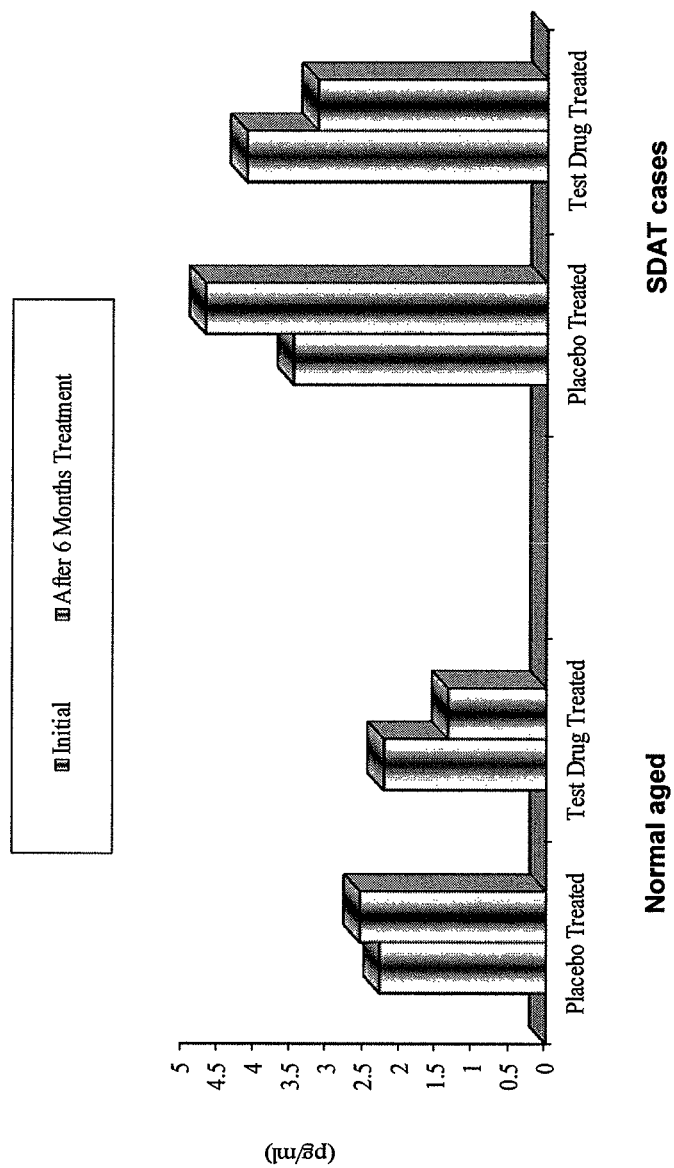
FIG. 9 is showing the effect of test drug on Interleukin-6 level in SDAT cases.

Results of the Effect of test drug on Interleukin-6 level in SDAT cases are shown in FIG. 9.

TABLE 10

Effect of test drug on TNF-α level in SDAT cases

| Treated groups | | TNF-α (pg/ml) | | | Comp. initial vs 6 months treatment |
|---|---|---|---|---|---|
| | | Initial | After 3 months | After 6 months | |
| Normal aged | P td (N = 62) | 364.97 ± 53.41 | 410.85 ± 64.17 | 459.42 ± 71.28 | P < 0.001 |
| | T td (N = 68) | 483.80 ± 85.64 | 422.90 ± 91.23 | 378.91 ± 48.42 | P < 0.001 |
| SDAT cases | P td (N = 71) | 994.75 ± 128.42 | 972.40 ± 128.75 | 983.73 ± 121.05 | P > 0.05 |
| | T td (N = 78) | 1124.06 ± 105.87 | 835.71 ± 128.45 | 744.55 ± 101.73 | P < 0.001 |

Figure 10:
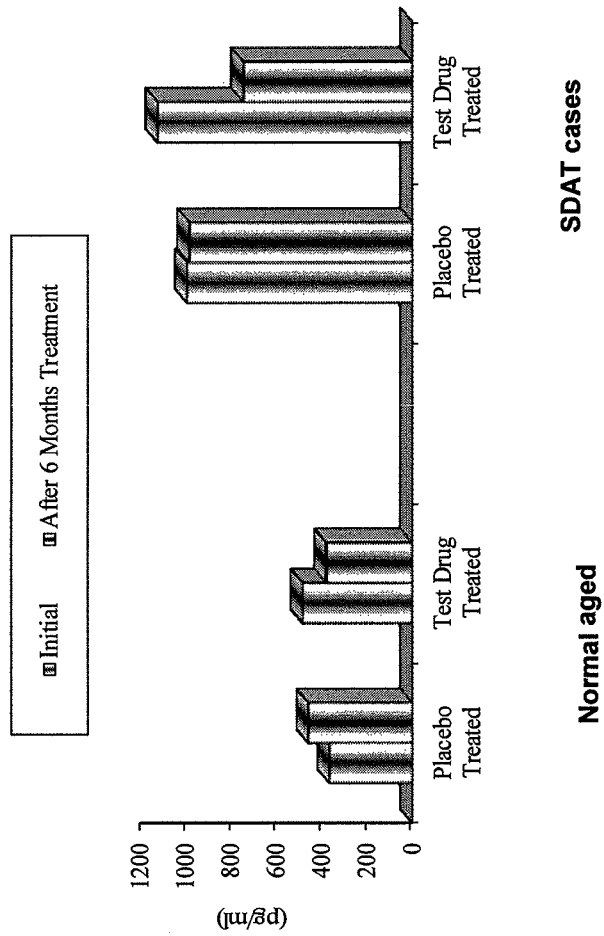
FIG. 10 is showing the effect of test drug on TNF-α level in SDAT cases.

Results of the Effect of test drug on TNF-α level in SDAT cases are shown in FIG. 10.

TABLE 11

Effect of test drug on Homocysteine level in SDAT cases

| Treated groups | | Homocysteine (mmol/L) | | | Comp. initial vs 6 months treatment |
|---|---|---|---|---|---|
| | | Initial | After 3 months | After 6 months | |
| Normal aged | P td (N = 62) | 21.99 ± 2.85 | 23.41 ± 3.52 | 20.90 ± 3.05 | P < 0.05 |
| | T td (N = 68) | 23.41 ± 2.75 | 21.06 ± 3.12 | 18.42 ± 3.29 | P < 0.001 |
| SDAT cases | P td (N = 71) | 38.42 ± 4.16 | 37.88 ± 3.96 | 39.42 ± 4.11 | P > 0.05 |
| | T td (N = 78) | 42.90 ± 5.62 | 34.82 ± 3.87 | 29.08 ± 4.16 | P < 0.001 |

Figure 11:
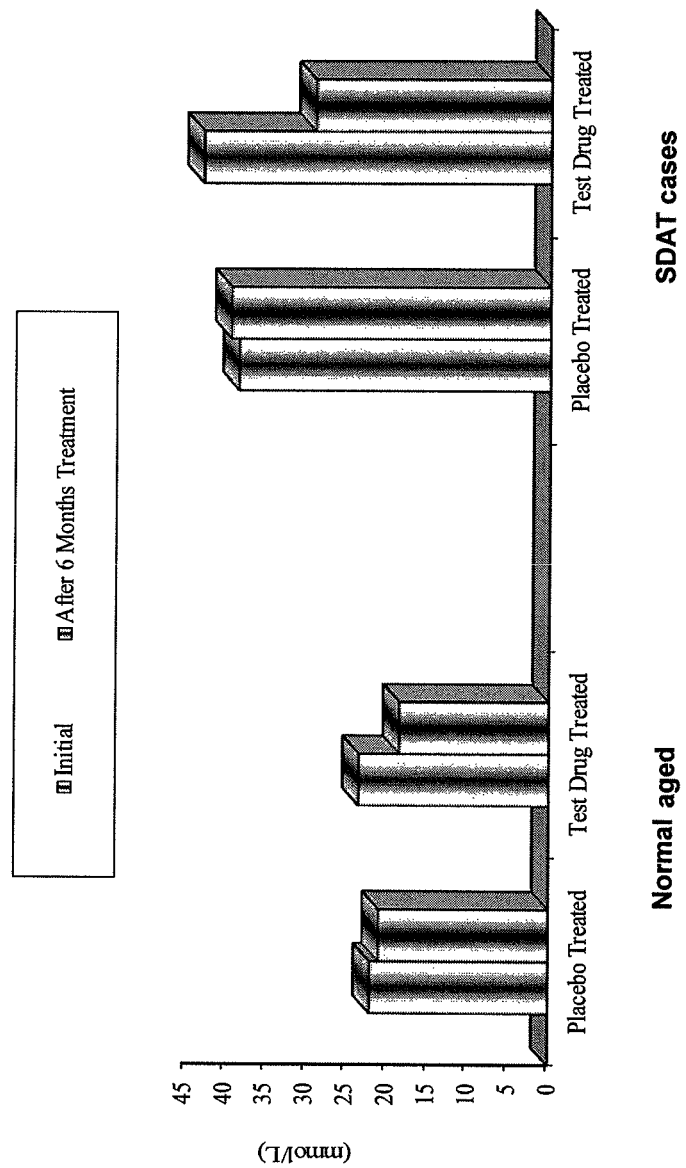
FIG. 11 is showing the effect of test drug on Homocysteine level in SDAT cases.

Results of the Effect of test drug on Homocysteine level in SDAT cases are shown in FIG. 11.

We claim:

1. A pharmaceutical capsule or tablet for the treatment of a neurodegenerative disorder consisting essentially of an effective amount of hydro-methanolic extracts of *Valeriana jatamansi, Curcuma longa*, and *Bacopa monnieri*;
wherein the ratio of the hydro-methanolic extracts of *Curcuma longa* to *Valeriana jatamansi* is 1:3 to 2:1, and the ratio of the hydro-methanolic extracts of *Bacopa monnieri* to *Valeriana jatamansi* is 1:1.8 to 2.5:1.

2. The pharmaceutical capsule or tablet as claimed in claim 1, wherein the extracts are from the plant parts:

| 1. | *Curcuma longa* (Haridra) | rhizome |
| 2. | *Valeriana jatamansi* (Tagar) | rhizome |
| 3. | *Bacopa monnieri* (Brahmi) | whole plant. |

3. The pharmaceutical capsule or tablet as claimed in claim 1, wherein the effective amount provides at least one of anti-oxidant activity, neuromodulatory activity, and restoring acetylcholine levels, thereby slowing the process of memory and learning deficit.

4. The pharmaceutical capsule or tablet as claimed in claim 1, wherein the effective amount provides neuromodulatory activity by regulating the neurotransmitters.

5. The pharmaceutical capsule or tablet as claimed in claim 1 wherein the effective amount provides a tranquilizing effect for the management of sleep disorders.

6. The pharmaceutical capsule or tablet as claimed in claim 1 wherein the effective amount provides a neuroprotective effect in ageing and neurodegenerative pathologies by ameliorating pathways selected from the group consisting of neuro-chemical modulation, mitochondrial dysfunction, antioxidant activity and reduction in neuroinflammation.

7. The pharmaceutical capsule or tablet as claimed in claim 1, wherein the effective amount elevates neuro-chemical contents in the brain thereby having neuromodulatory activity.

8. The pharmaceutical capsule or tablet as claimed in claim 1, wherein the effective amount provides anti-oxidant activity.

9. The pharmaceutical capsule or tablet as claimed in claim 1, wherein the effective amount provides anti-neuroinflammatory activity to reduce brain inflammation.

10. The pharmaceutical capsule or tablet as claimed in claim 1, wherein the effective amount provides anti-psychotic effects and improving behavioral disorders among demented patients.

11. The pharmaceutical capsule or tablet of claim 1, wherein the effective amount provides at least one of anti-oxidant activity; neuromodulatory activity; restoring acetylcholine levels thereby slowing the process of memory and learning deficit; regulation of neurotransmitters; a tranquilizing effect for the management of sleep disorders; a neuroprotective effect in ageing and neurodegenerative pathologies by ameliorating neuro-chemical modulation, mitochondrial dysfunction, antioxidant activity or reduction in neuro-inflammation; elevates neuro-chemical contents in the brain thereby having neuromodulatory activity; reducing brain inflammation; anti-psychotic effects; and improving behavioral disorders.

\* \* \* \* \*